(12) United States Patent
Takeda et al.

(10) Patent No.: US 10,893,846 B2
(45) Date of Patent: Jan. 19, 2021

(54) ULTRASOUND DIAGNOSIS APPARATUS

(71) Applicant: KONICA MINOLTA, INC., Tokyo (JP)

(72) Inventors: Yoshihiro Takeda, Hachioji (JP); Kazuya Takagi, Machida (JP); Jo Shikama, Hachioji (JP); Makoto Horiuchi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 1323 days.

(21) Appl. No.: 14/983,029

(22) Filed: Dec. 29, 2015

(65) Prior Publication Data

US 2016/0199025 A1 Jul. 14, 2016

(30) Foreign Application Priority Data

Jan. 9, 2015 (JP) .................................. 2015-002775
Dec. 21, 2015 (JP) .................................. 2015-248101

(51) Int. Cl.
*A61B 8/00* (2006.01)
*A61B 8/08* (2006.01)
*A61B 8/14* (2006.01)

(52) U.S. Cl.
CPC .......... *A61B 8/0841* (2013.01); *A61B 8/5207* (2013.01); *A61B 8/14* (2013.01); *A61B 8/5246* (2013.01); *A61B 8/54* (2013.01)

(58) Field of Classification Search
CPC ....... A61B 8/0841; A61B 8/5207; A61B 8/14; A61B 8/54
See application file for complete search history.

(56) References Cited

U.S. PATENT DOCUMENTS

| 9,226,729 | B2 * | 1/2016 | Tashiro | ................ | A61B 8/0841 |
| 9,326,749 | B2 * | 5/2016 | Okamura | .............. | A61B 8/0841 |
| 2014/0128728 | A1 * | 5/2014 | Baek | .................... | A61B 8/5207 600/424 |

FOREIGN PATENT DOCUMENTS

| JP | 5473853 B2 | 4/2014 |
| JP | 5486449 B2 | 5/2014 |

* cited by examiner

*Primary Examiner* — Joseph M Santos Rodriguez
(74) *Attorney, Agent, or Firm* — Holtz, Holtz & Volek PC

(57) ABSTRACT

An ultrasound diagnosis apparatus generates an ultrasound image of an inside of a subject on a basis of ultrasound signals which are reflected off at the inside of the subject and received. The apparatus includes a needle position specifier and a needle emphasis processor. With respect to each region in the ultrasound image, the needle position specifier obtains a deep region feature value relating to signal intensity in a region deeper than a region subject to judgment in relation to ultrasound signal distribution along an emission direction of an ultrasound emitted in a subject, and specifies a position of a puncture-needle which is inserted in the subject. The needle emphasis processor carries out a process for emphasizing the position of the puncture-needle which is specified in the ultrasound image.

15 Claims, 12 Drawing Sheets $(\rho 0, \theta 0)$

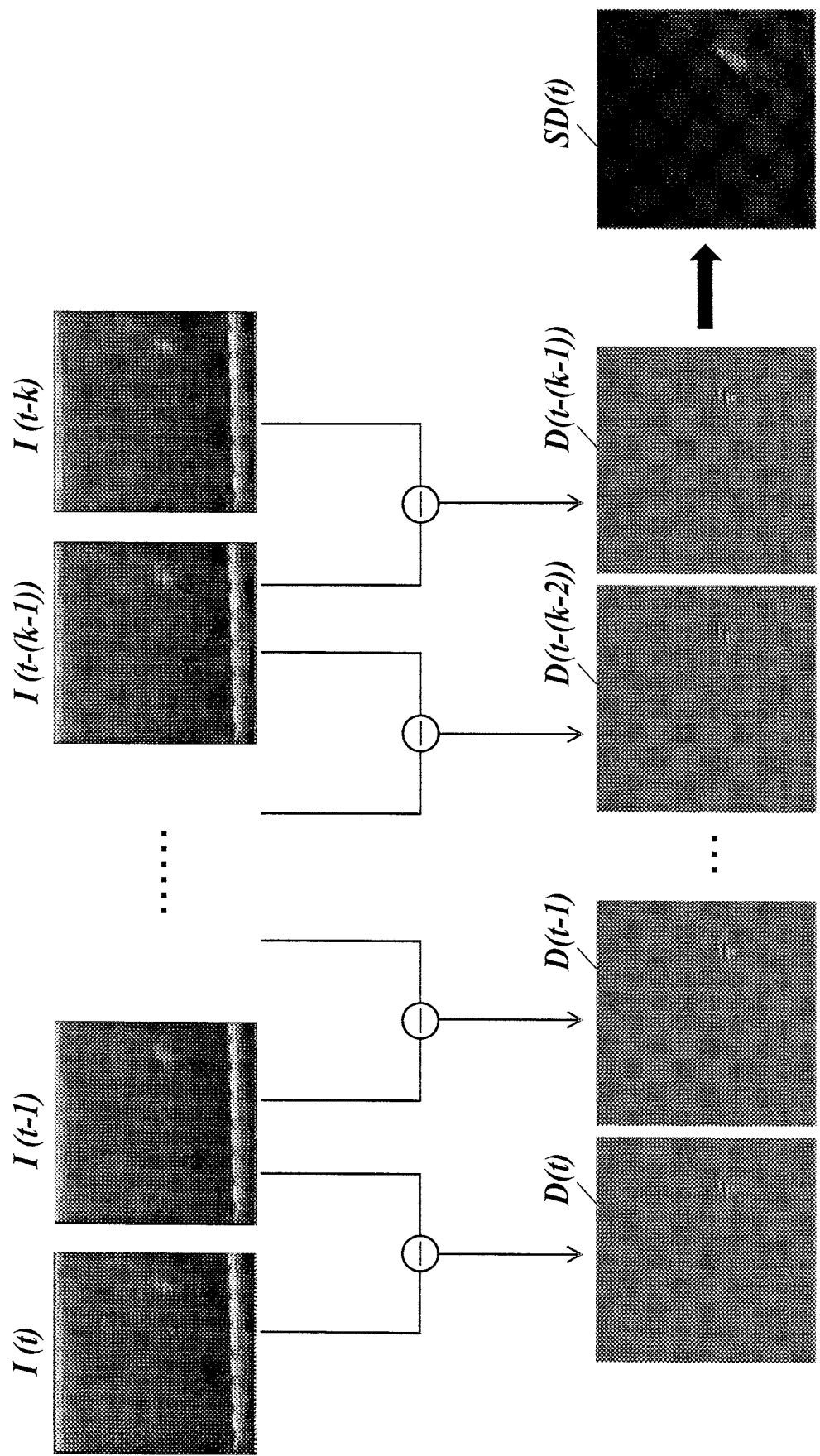

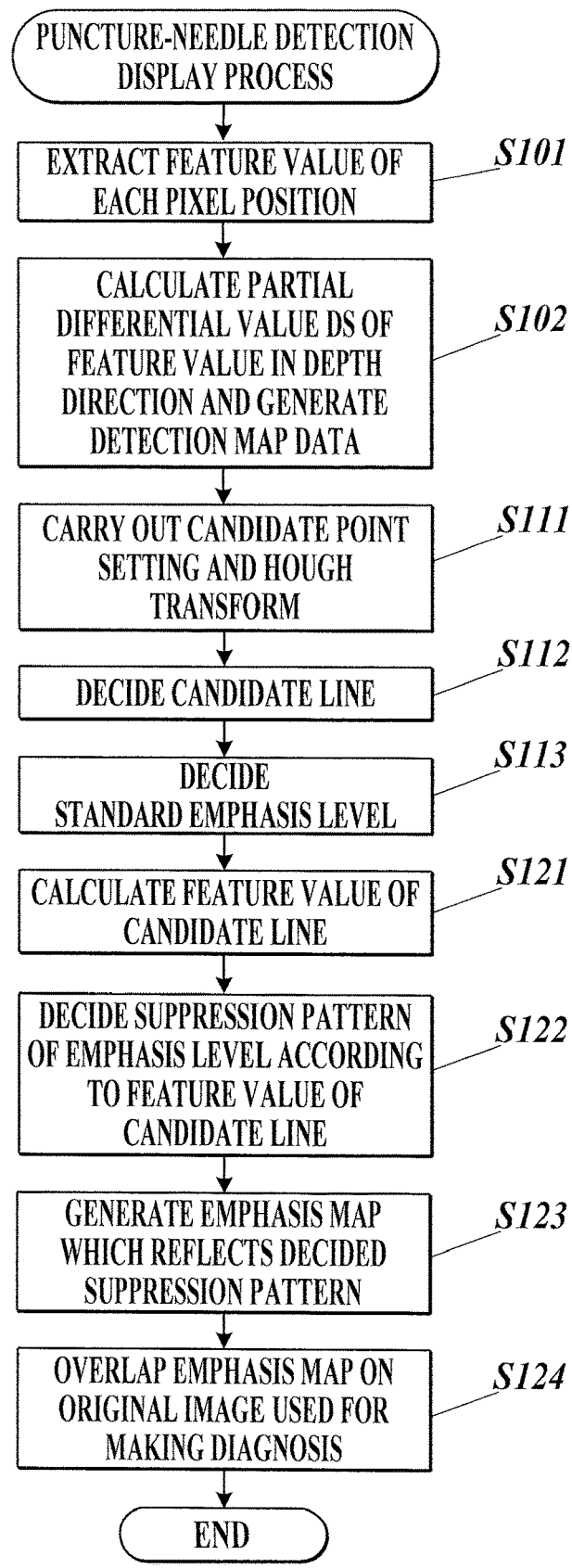

ULTRASOUND DIAGNOSIS APPARATUS

BACKGROUND OF THE INVENTION

1. Field of the Invention

The present invention relates to an ultrasound diagnosis apparatus.

2. Description of Related Art

Traditional ultrasound diagnosis apparatuses inspect the interiors of subjects through emitting ultrasounds into the subjects to receive reflected waves (echoes) in the subjects, and conducting predetermined processes to signal data on the received waves. Such ultrasound diagnosis apparatuses is used for various purposes, such as medical tests and treatments and inspection of the internal structures of buildings.

The use of the ultrasound diagnosis apparatuses is not limited to display of images based on the processed data on obtained reflected waves. The ultrasound diagnosis apparatuses are also used to identify and visualize the position of a puncture needle relative to a specific portion (target) in a subject during the sticking of the puncture needle into the target for sampling the target, discharging water from the target, or injecting or indwelling an agent or marker into the target. Such ultrasound image can facilitate rapid, certain, and ready treatment for the target in the subject.

However, the puncture-needle is very narrow and is usually inserted diagonally with respect to the subject. Therefore, there is a problem that the reflection light of the ultrasounds which are emitted perpendicularly into the subject is not sufficiently reflected in the transmission/reception direction of the ultrasounds and the puncture-needle does not appear clearly in the ultrasound image, and thus, it is difficult for a user to visually identify the puncture-needle.

In view of the above problem, there are various conventional techniques that enable a user to visually identify a puncture-needle clearly. One of such technique is to detect a puncture-needle by analyzing an ultrasound image and emphasizing the puncture-needle to be displayed. JP 5,473,853 discloses a technique to perform a puncture-needle emphasis-processing by obtaining information relating to the insertion direction of the puncture-needle and utilizing a filter that emphasize an edge of brightness that extends in the insertion direction in the ultrasound image. Further, JP 5,486,449 discloses a technique to specify the position of a puncture-needle by detecting a high illumination region that appears in the form of straight line in an ultrasound image and specifying the tip of the puncture-needle on the basis of the illumination distribution on the straight line.

However, in order to obtain information such as the insertion angle of a puncture-needle, additional structure other than the conventional structure is needed and the process can be time-consuming. Furthermore, in the conventional detection technique, there is a problem that an illumination distribution in the form of straight line other than the puncture-needle is likely to be detected.

SUMMARY OF THE INVENTION

An object of the invention is to provide an ultrasound diagnosis apparatus which can detect a puncture-needle easily and accurately.

In order to realize the above object, according to a first aspect of the present invention, there is provided an ultrasound diagnosis apparatus which generates an ultrasound image of an inside of a subject on a basis of ultrasound signals which are reflected off at the inside of the subject and received, including:

a needle position specifier which, with respect to each region in the ultrasound image, obtains a deep region feature value relating to signal intensity in a region deeper than a region subject to judgment in relation to ultrasound signal distribution along an emission direction of an ultrasound emitted in a subject, and which specifies a position of a puncture-needle which is inserted in the subject; and a needle emphasis processor which carries out a process for emphasizing the position of the puncture-needle which is specified in the ultrasound image.

Preferably, in the ultrasound diagnosis apparatus, the needle position specifier sets a value relating to rate of variability of the deep region feature value in the emission direction as a predetermined feature amount, and specifies the position of the puncture-needle on a basis of the predetermined feature amount.

Preferably, in the ultrasound diagnosis apparatus, the needle position specifier obtains the deep region feature value and a shallow region feature value relating to signal intensity in a region shallower than the region subject to judgment, and specifies the position of the puncture-needle which is inserted in the subject on a basis of the deep region feature value and the shallow region feature value.

Preferably, in the ultrasound diagnosis apparatus, the needle position specifier obtains a maximum value of values corresponding to signal intensity at individual regions deeper than the region subject to judgment as the deep region feature value.

Preferably, the ultrasound diagnosis apparatus further includes:

a transmitter/receiver which performs transmission and reception of the ultrasound signals; and a transmission/reception controller which controls a transmission/reception range of the transmitter/receptor, wherein the transmission/reception controller makes a width where the ultrasounds are to be emitted in a width direction perpendicular to a length direction of the puncture-needle narrower when obtaining the ultrasound image in which the needle position specifier specifies the position of the puncture-needle as compared with that of when obtaining the ultrasound image in which the position of the puncture-needle is not to be specified.

Preferably, in the ultrasound diagnosis apparatus, shape of the specified puncture-needle is a straight line.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 10 is a view showing the fourth example relating to estimation of the tip position of a puncture-needle;

FIG. 12 is a flowchart showing a controlling procedure of the puncture-needle detection and emphasis processing;

DETAILED DESCRIPTION OF THE PREFERRED EMBODIMENT

Hereinafter, an embodiment of the present invention will be described with reference to the drawings. Though various technical limitations which are preferable to perform the present invention are included in the after-mentioned embodiment, the scope of the invention is not limited to the following embodiment and the illustrated examples.

First Embodiment

The first embodiment of an ultrasound diagnosis apparatus according to the present invention will be described.

Figure 1:
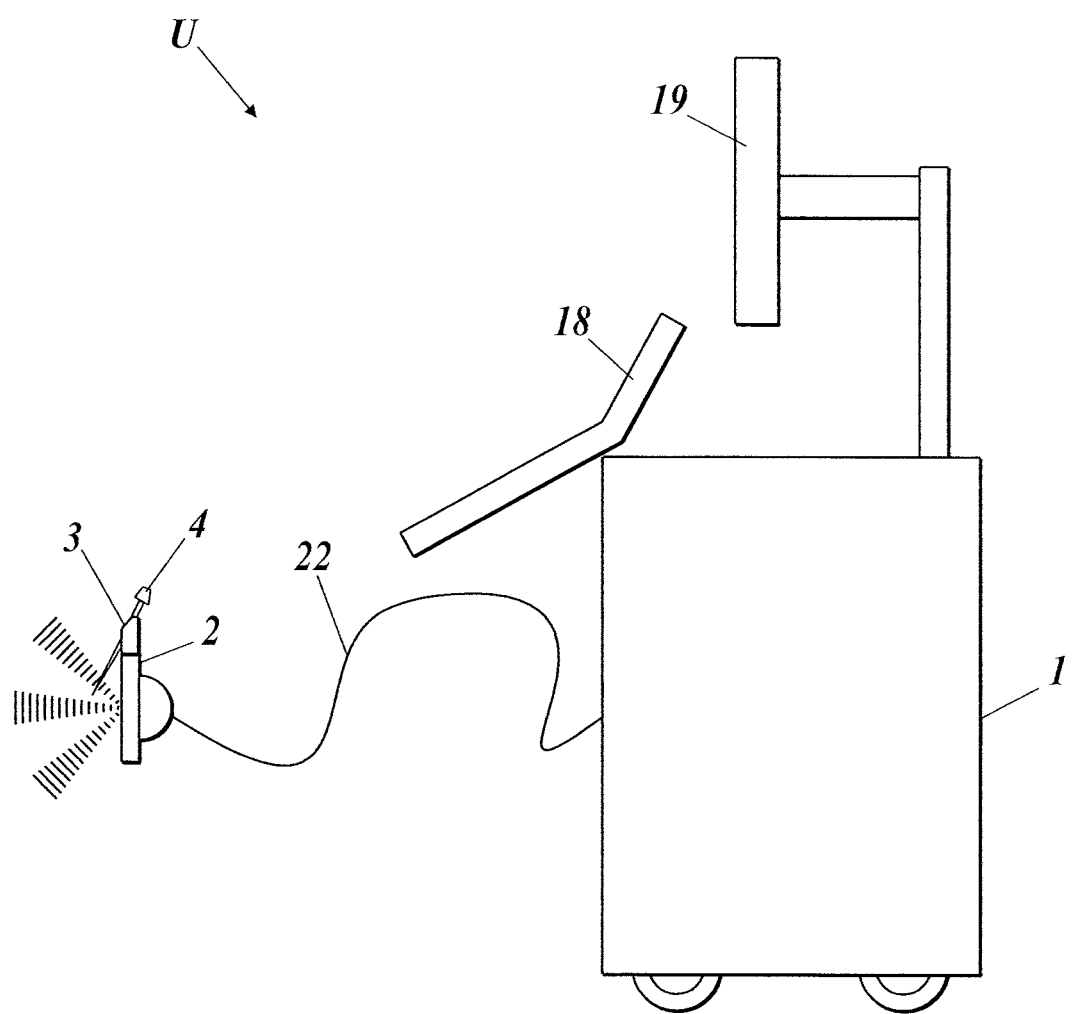
FIG. 1 illustrates the entire configuration of an ultrasound diagnosis apparatus according to an embodiment of the invention.
Figure 2:
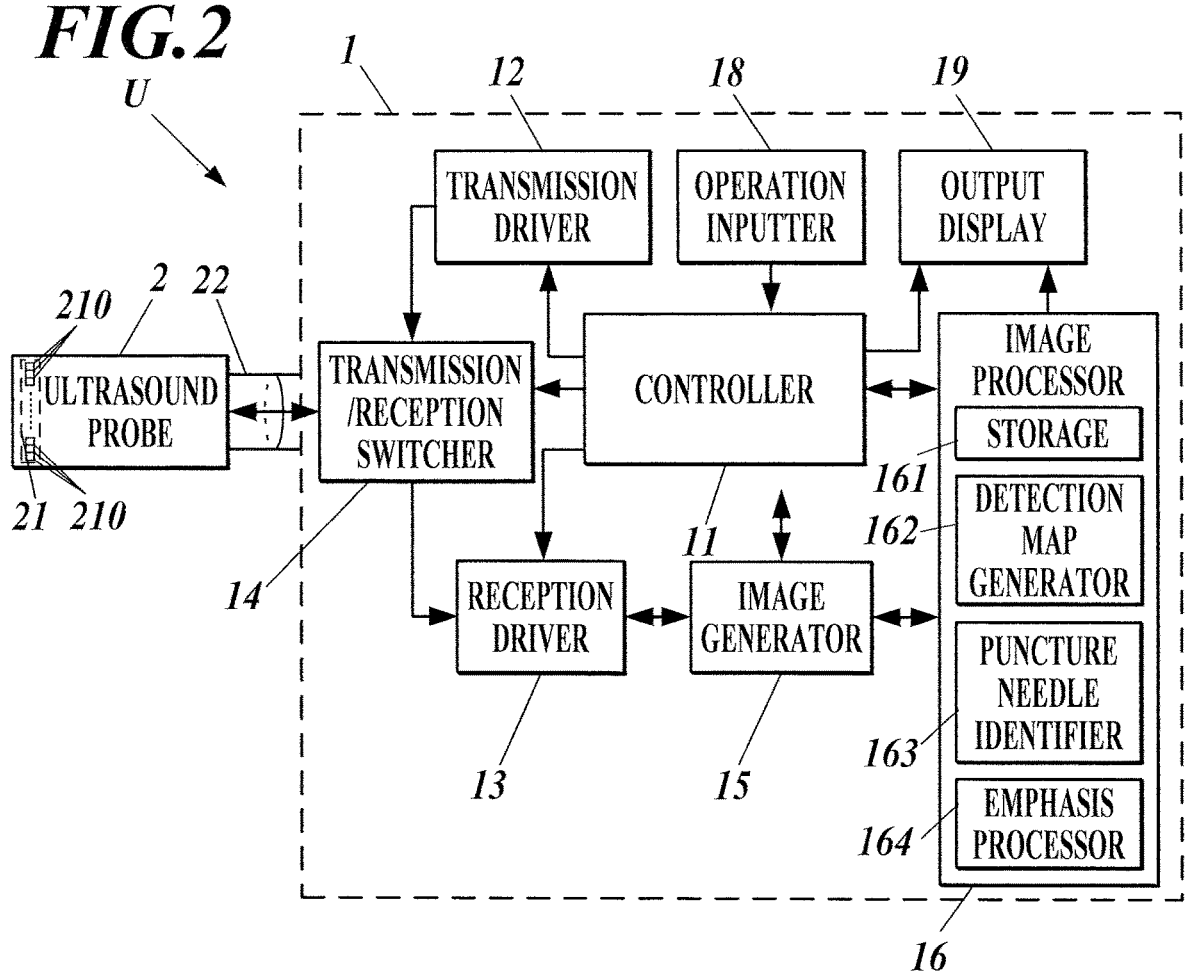
FIG. 2 is a block diagram illustrating the internal configuration of the ultrasound diagnosis apparatus.

FIG. 1 illustrates the entire configuration of an ultrasound diagnosis apparatus U according to the first embodiment. FIG. 2 is a block diagram illustrating the internal configuration of the ultrasound diagnosis apparatus U.

With reference to FIG. 1, the ultrasound diagnosis apparatus U includes an apparatus body 1, an ultrasound probe 2 (transmitter/receiver) connected to the apparatus body 1 via a cable 22, an attachment 4 (puncturing mechanism) mounted to the ultrasound probe 2, and a puncture needle 3.

The puncture needle 3 is elongated and hollow, and is configured to be stuck into a subject at an angle defined by the attachment 4. The puncture needle 3 may be replaced with another one having any appropriate thickness, length, and tip shape depending on a target (specimen) to be sampled and the type and volume of an agent to be injected.

The attachment 4 retains the puncture needle 3 in the set orientation (direction). The attachment 4 is mounted to a side of the ultrasound probe 2 and can appropriately change the orientation of the puncture needle 3 depending on a desired angle of the puncture needle 3 relative to the subject.

Alternatively, the ultrasound probe 2 may be directly provided with a guide section for retaining the puncture needle 3 in the puncture direction, in place of the attachment 4.

The apparatus body 1 includes an operation input unit 18 and an output display 19. With reference to FIG. 2, the apparatus body 1 further includes a controller 11 (transmission-reception controller), a transmission driver 12, a reception driver 13, a transmission-reception switcher 14, an image generator 15, and an image processor 16.

The controller 11 of the ultrasound diagnosis apparatus 1 carries out the series of operations of outputting a driving signal to the ultrasound probe 2 to output ultrasounds, obtaining a received signal relating to ultrasound reception from the ultrasound probe 2 to carry out various types of processes, and displaying the results in a display screen of the output display 19 as needed on the basis of an operation signal from an input device such as a key board or a mouse of the operation inputter 18 and a detection signal from a touch sensor which detects a touching operation to the display screen which are made by input operation from outside.

The controller 11 includes a central processing unit (CPU), a hard disk drive (HDD), and a random access memory (RAM). The CPU reads various programs from the HDD and loads the programs in the RAM, to comprehensively control the operations of the individual components of the ultrasound diagnosis apparatus U under the instructions of the programs. The HDD stores a control program for operating the ultrasound diagnosis apparatus U, various processing programs, and various types of setting data. Alternatively, the programs and setting data may be rewritably stored in an auxiliary storage device including a non-volatile memory, such as a flash memory including a solid state drive (SSD), instead of the HDD. The RAM is a volatile memory, for example, an SRAM or a DRAM. The RAM provides the CPU with a working memory space and stores temporary data.

The transmission driver 12 outputs pulse signals to be supplied to the ultrasound probe 2 on the basis of control signals input from the controller 11, so that the ultrasound probe 2 generates ultrasounds. The transmission driver 12 includes, for example, a clock generating circuit, a pulse generating circuit, a pulse width setter, and a delay circuit. The clock generating circuit generates clock signals for determining the transmission timing and frequency of pulse signals. The pulse width setter sets the waveform (shape), voltage amplitude and pulse width of a transmission pulse which is to be output from the pulse generating circuit. The pulse generating circuit generates transmission pulses on the basis of the setting of the pulse width setter and outputs the transmission pulses to different wiring paths according to individual transducers 210 of the ultrasound probe 2. The delay circuit counts the clock signals which are to be output from the clock generating circuit, and when the set delay time elapsed, the delay circuit makes the pulse generating circuit generate transmission pulses and output the generated transmission pulses to individual wiring paths.

The reception driver 13 is a circuit that obtains reception signals input from the ultrasound probe 2 under the control of the controller 11. The reception driver 13 includes, for example, an amplifier, an analog-digital conversion circuit, and a phasing addition circuit. The amplifier is a circuit that amplifies the reception signals generated in response to the ultrasounds received by the respective oscillators 210 of the ultrasound probe 2 by a predetermined amplification factor. The analog-digital conversion circuit converts the amplified reception signals into digital data at a predetermined sampling frequency. The phasing addition circuit adjusts the time phases of the digitized reception signals by adding a delay time to each of the signals for each of the wiring paths corresponding to the respective oscillators 210 and then adds these signals together, namely, performs phasing addition, to generate sound-ray data.

The transmission-reception switcher 14 performs switching between a mode of causing the transmission driver 12 to output drive signals to the oscillators 210 and thus controlling the oscillators 210 to emit (transmit) ultrasounds, and a mode of causing the reception driver 13 to output reception signals to receive signals related to the ultrasounds emitted from the oscillators 210, under the control of the controller 11.

The image generator 15 creates diagnostic images (ultrasound images) based on the received ultrasound data (ultrasound signal). The image generator 15 detects sound-ray data input from the reception driver 13 through envelope detection to acquire signals. The image generator 15 may optionally execute logarithmic amplification, filtering (e.g., low-path filtering or smoothing), and/or enhancement on the acquired signals. The image generator 15 creates, as one of the diagnostic images, frame image data in a B-mode display which is represented by the luminance signals depending on the intensities of the acquired signals and shows the two-dimensional structure (structure inside the subject) across the plane including the transmission direction (the incidence direction, the depth in the subject) of the signals and the scanning direction of ultrasounds transmitted from the ultrasound probe 2. The image generator 15 may adjust the dynamic range for display and execute gamma correction. The image generator 15 may include a CPU and a RAM dedicated to the image creation. Alternatively, the image generator 15 may include a hardware configuration dedicated to the image creation on a substrate (e.g., application-specific integrated circuit (ASIC)). Alternatively, the image generator 15 may execute processes of the image creation using the CPU and the RAM of the controller 11.

The image processor 16 carries out various types of processes for detecting a puncture-needle 3 in the generated image used for making diagnosis and emphasizing and displaying the puncture-needle 3. Further, the image processor 16 temporarily stores and maintains the data of the puncture-needle 3 until the display timing. The image processor 16 includes a storage 161, a detection map generator 162, a puncture-needle identifier 163, an emphasis processor 164 (needle emphasis processing section) and the like.

The needle position specifier includes the detection map generator 162 and the puncture-needle identifier 163.

The storage 161 stores a predetermined number of frames of latest diagnostic image data (frame image data), which are processed by the image generator 15 to be used for real-time or substantially real-time display. The storage 161 is a volatile memory, such as a dynamic random access memory (DRAM). Alternatively, the storage 161 may be any high-speed rewritable non-volatile memory. The diagnostic image data stored in the storage 161 is read under the control of the controller 11, to be transmitted to the output display 19 or to be output to the outside of the ultrasound diagnosis apparatus U via a communication unit (not shown). If the output display 19 is in a television system, the scan format of the diagnostic image data should be converted by a digital signal converter (DSC) provided between the storage 161 and the output display 19 before the output. The storage 161 stores data of an image used for making diagnosis which is ordered to be stored by the input operation to the operation inputter 18 made by a user of the ultrasound diagnosis apparatus U during the operation of the ultrasound diagnosis apparatus U, during a predetermined period of time, or until it is deleted by an input operation of the user.

The detection map generator 162 generates detection map data used for identifying the puncture-needle 3 by the puncture-needle identifier 163 and specifying its position. The detection map data will be described later.

The puncture-needle identifier 163 identifies the puncture-needle 3 by using the detection map data generated by the detection map generator 162. The puncture-needle identifier 163 stores the record of puncture-needle positions that are identified up to present and for example, can calculate the transition speed and transition direction (disposition vector) of the positions. In such case, the puncture-needle identifier 163 can calculate the next estimate position of the puncture-needle 3 on the basis of the positions of the puncture-needle 3 and the disposition vectors in advance and can use the estimate position in identifying.

The emphasis processor 164 carries out processes for emphasizing the position of the identified puncture-needle 3 in the displayed image. The emphasis processor 164 determines the content of the emphasis process according to the specified position of the puncture-needle 3 which is identified by the puncture-needle identifier 163 and the level of certainty of the identification, performs the emphasis process on the image used for making diagnosis and stores the image in the storage 161.

The detection map generator 162, the puncture-needle identifier 163 and the emphasis processor 164 can share the CPU and the RAM of the image processor 16 or each of them can be provided with its exclusive CPU and RAM. Alternatively, various processes relating to the detection map generator 162, the puncture-needle identifier 163 and the emphasis processor 164 can be carried out by the CPU and RAM of the controller 11.

The operation inputter 18 includes a push button switch, a keyboard, a mouse, a trackball, a touch sensor on a display screen and any combination of the above. The operation inputter 18 converts an input operation made by a user into an operating signal and inputs the signal in to the ultrasound diagnosis apparatus 1.

The output display 19 includes a display screen and a driving unit therefor. The display screen may use any display system, for example, a liquid crystal display (LCD), an organic electroluminescent (EL) display, an inorganic EL display, a plasma display, or a cathode-ray tube (CRT) display. The output display 19 generates drive signals for the display screen (individual display pixels) on the basis of the control signals output from the CPU of the image generator 15 and the image data processed by the image processor 16, and thus causes the display screen to display a menu and a status for ultrasound diagnosis and measured data based on the received ultrasounds. The output display 19 may also be equipped with an LED lamp indicating an ON/OFF state of the power.

The operation input unit 18 and the output display 19 may be integrated with a housing of the apparatus body 1, or may be connected to the apparatus body 1 from the outside thereof via a RGB cable, USE cable or HDMI (registered trademark) cable. In the apparatus body 1 equipped with an operation input terminal and a display output terminal, these terminals may be respectively connected to traditional peripheral devices for operation and display.

The ultrasound probe 2 oscillates ultrasounds (approximately 1 to 30 MHz in this embodiment) and emits the ultrasounds to the subject, such as a living body. The ultrasound probe 2 also functions as an acoustic sensor to receive the reflected waves (echoes) of the emitted ultrasounds that are reflected from the subject and to convert the echoes into electrical signals. The ultrasound probe 2 includes an oscillator array 21 (transmitter/receiver) composed of an array of multiple oscillators 210 for transmitting and receiving the ultrasounds, and a cable 22.

The cable 22 includes a connector (not shown) to the apparatus body 1 at an end, so as to removably connect the ultrasound probe 2 to the apparatus body 1. The user brings an ultrasound transmission/reception surface of the ultrasound probe 2, namely, a surface from which the oscillator array 21 emits the ultrasounds, into contact with the subject with a predetermined pressure, and activates the ultrasound diagnosis apparatus U for ultrasound diagnosis.

Here, the ultrasound diagnosis apparatus 1 and the ultrasound probe 2 can be connected by a wireless communication method using infrared, radio wave or the like other than the connection method using the cable 22.

The transducer array 21 is an array of a plurality of transducers 210 each of which including a piezo-electric device having a piezoelectric material and two electrodes respectively provided at two ends of the piezoelectric material where electric charges appear due to the deformation (expansion and contraction) of the piezoelectric material. For example, the transducer array 21 is a one-dimensional array in a predetermined direction (scanning direction). By voltage pulses (pulse signals) being sequentially supplied to the transducers 210, each piezoelectric material deforms according to the electrical field produced in the piezoelectric material and an ultrasound is produced. Further, when an ultrasound of a predetermined frequency band enters in to a transducer 210, the thickness of its piezoelectric material changes (oscillates) due to the sound pressure leading to production of electrical charge according to the change amount. Then, the electrical charge is converted into an electronic signal according to its amount and the electronic signal is output.

Next, a detection method of the puncture-needle 3 of the ultrasound diagnosis apparatus U according to the embodiment will be described in detail.

Figure 3:
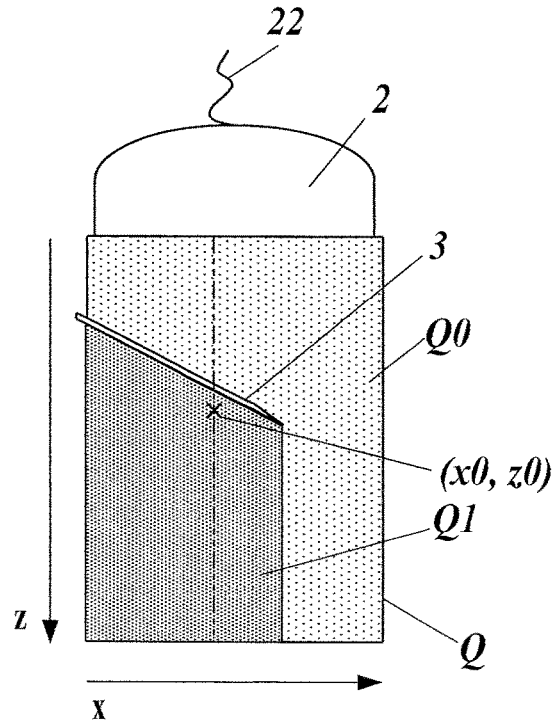
FIG. 3 is a schematic view used for explaining a way of calculating detection map data relating to puncture-needle detection.
Figure 4A:
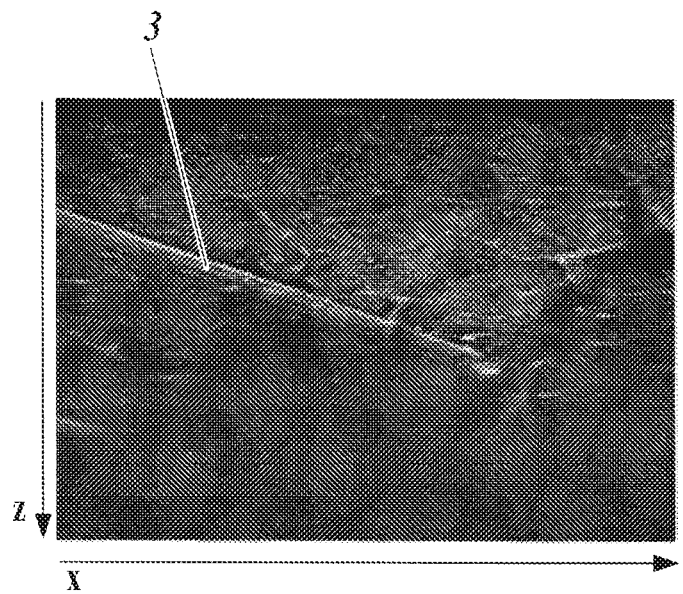
FIG. 4A is a view showing an example of an ultrasound image used for puncture-needle detection.
Figure 4B:
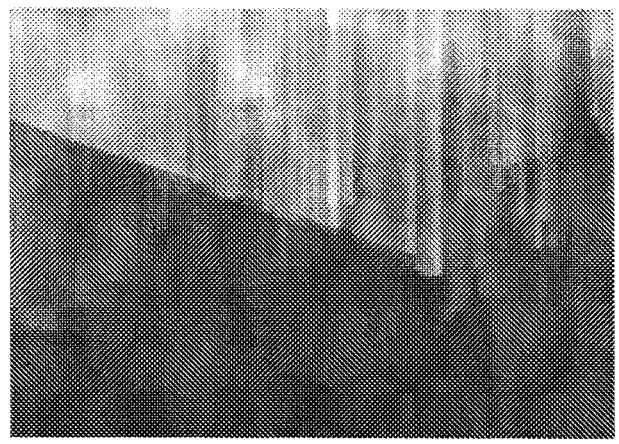
FIG. 4B is a view showing a calculation example of a feature amount relating to the puncture-needle detection.
Figure 4C:
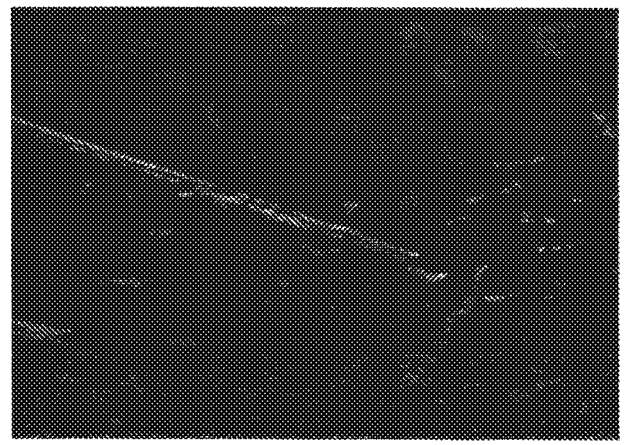
FIG. 4C is a view showing a calculation example of puncture-needle detection map data.

FIG. 3 is a schematic view used for explaining a calculation of detection map data relating to detection of a puncture-needle. FIGS. 4A to 4C are views showing calculation examples of puncture-needle detection map data.

Here, ultrasounds are input downwardly (z direction) from the ultrasound probe 2 at the upper side in the images, and the ultrasounds reflected off at inside of a subject Q which are transmitted upward are received and detected.

With respect to a puncture-needle 3, according to its thickness and inclination, a great part of the ultrasound component is reflected in a direction other than the upward direction (in FIG. 3, in in the upper diagonally right direction) and only a small part of the ultrasound component is transmitted downward. As a result, the region Q1 below the puncture-needle 3 is a region that is to be in the shade of the puncture-needle 3 (acoustic shadow) where the ultrasound component to be reflected off at the region Q1 is relatively small as compared with that in the region Q0. In the ultrasound diagnosis apparatus U of the embodiment, the puncture-needle 3 is detected by identifying the border of the region Q0 and the region Q1.

At this time, when the ultrasounds travel along both sides of the puncture-needle 3 (orthogonal (front and back) direction with respect to the display surface of FIG. 3), the drop in reflection intensity in the region below the puncture-needle 3 is to be relatively small. Therefore, it is desired that the transmission/reception width of ultrasounds is not extremely wider as compared with the width of the puncture-needle 3.

In order to identify the border, first, a brightness value s (x0, z0) (x0 and z0 are integers of 0 or greater) according to the reflection intensity at each pixel position (for example, (x0, z0)) is analyzed based on the brightness value distribution along the entering direction (z direction) of the ultrasound with respect to the pixel position (the region subject to judgment). Here, a statistical representative value of the reflection intensities obtained at individual pixel positions that are in the region of the subject Q shallower ($z \leq z0$) than the pixel position (x0, z0), here, the average value $sa = \Sigma s (x0, z \leq z0)/(z0+1)$ (shallow region feature value) is calculated. With respect to the pixel positions that are in the region shallower than the border position (the side where z is smaller), this average value sa increases temporarily as the high brightness region is to be included. With respect to the pixel positions that are in the region deeper than the border position (the side where z is greater), this average value sa gradually decreases as the percentage of the region having low overall brightness increases. Further, at the position where the puncture-needle 3 is not inserted, the average value sa does not change greatly since the overall density does not decrease. Alternatively, another statistical value representing the pixel values in the shallow region of the subject Q, for example, the median $s_{median}$ (s(x0, $z \leq Z0$)) or the mode $s_{mode}$ (s(x0, $z \leq 0$) g) (median of a brightness value range) of brightness appearance distribution (appearance ratio) of each predetermined brightness value range g can be calculated and used as the shallow region feature value.

With respect to each pixel position (x0, z0), the maximum value sm=max (s (x0, $z \geq z0$)) (deep region feature value) of the reflection intensities obtained at pixel positions that are in the region of the subject Q deeper z0) than the pixel position is calculated. If a high brightness point exists in the shallow region of the subject Q, the maximum value sm discontinuously drops with the high brightness point being the border as the coordinate z0 in the depth direction increases. At the position of the puncture-needle 3, such discontinuous drop occurs at high possibility.

Therefore, at each pixel position (x0, z0), the feature amount sc=sa−sm which is the difference of the average value sa and the maximum value sm becomes a large value due to s0 increasing and sm decreasing at the position of the puncture-needle 3. Further, the partial differential value (the differential value with the adjacent pixel position) ds (x0, z0)=∂s/∂z of the feature amount sc in the z direction, here, simply sc(x0, z0)−sc(x0, z0−1) is calculated for each x0, z0 and this is the detection map data.

With respect to the image used for making diagnosis shown in FIG. 4A, the two-dimensional map of the feature amounts sc is obtained as shown in FIG. 4B and the detection map data is obtained as shown in FIG. 4C.

When the partial differential values ds are obtained for all of the pixel positions, next, the puncture-needle 3 is to be detected by using the detection map data. In such detection, a well-known conventional detection method, specifically, the method for detecting a straight line in the image data is used. Here, for example, Hough transform is used.

FIGS. 5A to 5D are views showing detection examples of a straight line corresponding to a puncture-needle 3 on the basis of the detection map data obtained as in FIG. 4C.

Figure 5A:
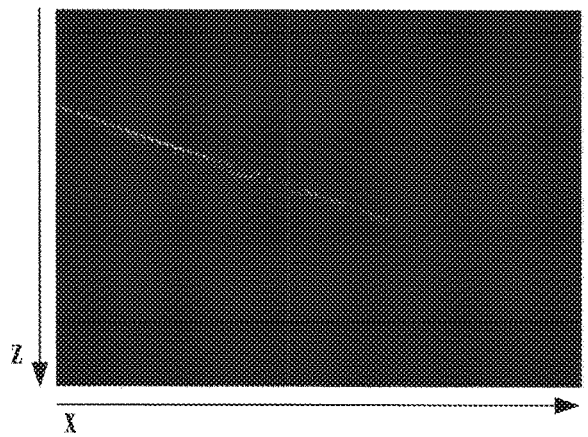
FIG. 5A is a view showing an example where candidate points of a puncture-needle are extracted on the basis of the detection map data.

The partial differential values ds which are values at individual points on the detection map data obtained as in FIG. 4C are binarized with a predetermined threshold, for example, and as shown in FIG. 5A, the points of the threshold value or greater (the points fulfilling a predetermined condition) are determined as the candidate points $(x_i, z_i)$ (pixels in the detection candidate region) of the puncture-needle 3. The candidate points $(x_i, z_i)$ usually cannot clearly indicate the range (needle position range) corresponding to the overall position of the puncture-needle 3 in the ultrasound image, and the range is often times scatterly specified.

Figure 5B:
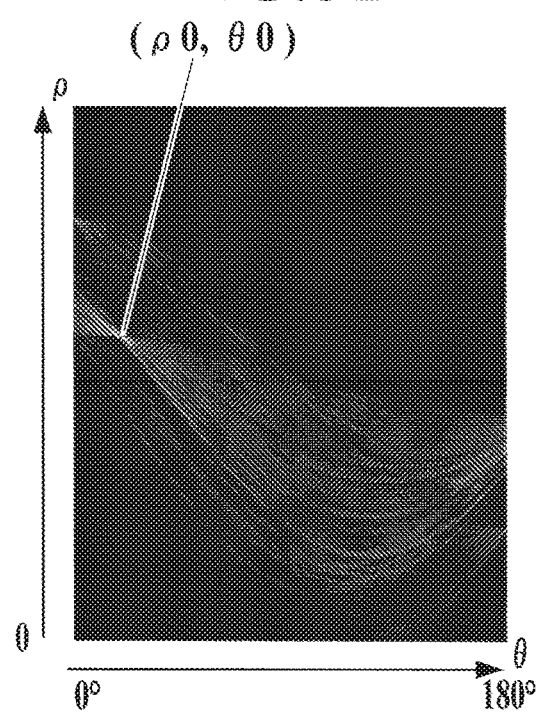
FIG. 5B is a view showing an example of straight line detection by Hough transform.
Figure 5C:
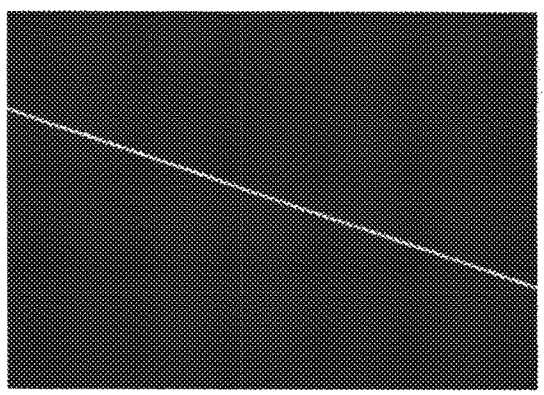
FIG. 5C is a view showing an example of a straight line corresponding to the puncture-needle detected in the detection map data.

Next, since the puncture-needle 3 is usually in the form of straight line, a straight line is to be detected by Hough transform, the straight line being where the candidate points are gathered thereon according to the form of the puncture-needle 3 (FIG. 5B). If each candidate point $(x_i, z_i)$ is shown as $\rho = x_i \cos\theta + z_i \sin\theta$ using the length variable ρ and the angle variable e, the combination of (ρ, θ) that fulfills the above equation shows the length of a perpendicular line from the point of origin to the straight line that passes the candidate point $(x_i, z_i)$ and the angle formed by the x axis and the straight line. Therefore, the point (ρ0, θ0) that collects the most votes from the candidate points $(x_i, z_i)$ shows the plausible straight line (candidate line) that passes the candidate points (FIG. 5C).

As a method for detecting a line segment and not a straight line, there is known a method called probabilistic Hough transform. In the probabilistic Hough transform, a candidate line is detected by Hough transform from a group of points which are randomly selected, and then, an existing range on the candidate line of the selected points is confirmed. In such way, by specifying the start point and the end point on the candidate line, as a result, a line segment (length) can be detected.

At this time, in a case where candidate points lined to form a straight line other than the puncture-needle 3 exist, the candidate line does not have to be narrowed down to one and there can be a plurality of candidate lines. Further, in a case where the position of the puncture-needle 3 can be estimated in advance on the basis of another method, a candidate line of the puncture-needle 3 can be selected among a plurality of candidate lines on the basis of the estimation.

Figure 5D:
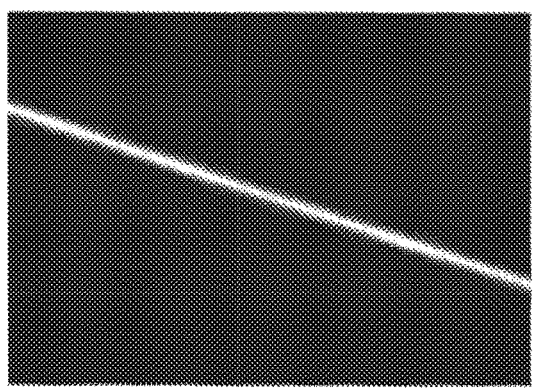
FIG. 5D is a view showing an example of emphasizing the straight line corresponding to the puncture-needle detected in the detection map data.

When the candidate line is detected, the emphasis level of the candidate line is determined according to the accuracy of the candidate line (FIG. 5D). That is, even if there remains a plurality of candidate lines, the emphasis level can be changed according to their possibility of matching to the puncture-needle 3, the emphasis level being different between low possibility and high possibility.

Next, the emphasis display of the puncture-needle 3 will be described.

In the ultrasound diagnosis apparatus U of the embodiment, emphasis display of the puncture-needle 3 is carried out by overlapping the emphasis display of the range where the puncture-needle plausibly exists on the selected candidate line on the image used for making diagnosis, the range being emphasized according to the level of plausibility.

Figure 6:
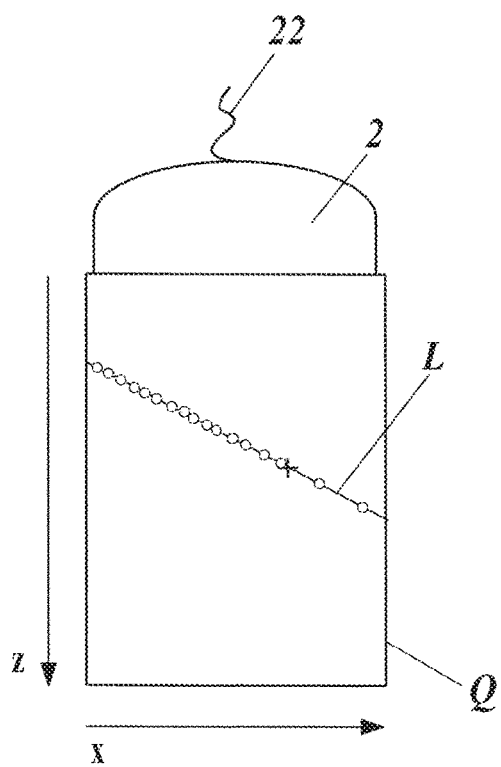
FIG. 6 is a view used for explaining an emphasis-processing of a puncture-needle.

FIG. 6 is a diagram used for explaining the emphasis process of the puncture-needle 3.

As described above, the two ends are not specified in the candidate line L which is selected by using Hough transform. Therefore, the tip position of the puncture-needle 3 cannot be specified. Further, the tip portion of the puncture-needle 3 can be difficult to identify since great amount of ultrasounds are dispersed and the reflection waves are even more less as compared with the other parts of the puncture-needle 3 due to the shape thereof. Further, in a case where there exists a noise or another structure that can reflect the ultrasounds in front of the tip portion, the position of the noise or another structure may be mistakenly recognized as the tip and the emphasis display may be an incorrect emphasis display different from the correct range. Thus, in the ultrasound diagnosis apparatus U of the embodiment, on the basis of the distribution condition of the candidate points used for selecting the candidate line L, especially the gathering condition (the center position of the gathering, the level of gathering, etc.), the emphasis display (emphasis suppression) is carried out by changing the level of emphasis in the plausible range of puncture-needle 3.

In the diagram shown in FIG. 6, the candidate points schematically shown in circles (o) are distributed on the candidate line L gathering toward the left side thereof. Further, there are fewer candidate points at the area near the actual tip position of the puncture-needle 3 shown by the plus sign (+) as compared with the area near the left end, and a few candidates points exist in front (right side) of the tip position.

Here, first, with respect to all of the candidate points $(x_i, z_i)$ ($1 \leq i \leq N$) on the candidate line, each candidate point is weighted with the feature amount $\omega_i = sc(x_i, z_i)$ at the candidate point $(x_i, z_i)$, and the weighting average position $(x_c, z_c)$ is calculated. That is, the weighting average position $(x_c, z_c)$ is obtained by $x_c = \Sigma(\omega_i \cdot x_i)/\Sigma(\omega_i)$ $z_c = \Sigma(\omega_i \cdot z_i)/\Sigma(\omega_i)$ by using N candidate points $(x_i, z_i)$ that fulfill $1 \leq i \leq N$ and N feature amounts $\omega_i$. With setting the weighting average position as the standard, the emphasis level is decreased with a predetermined filter. As the filter, although there is no limitation, window functions such as Gaussian window, Hanning window or the like is used, for example. The window width can be the length of the candidate line in the image used for making diagnosis irrelevant to the actual distribution of candidate points or can be a value specified by the variance (standard deviation) of the candidate points on the candidate line. The variance can be individually calculated for the left side and the right side of the weighting average position. Alternatively, skewness, kurtosis and the like can be obtained in addition to variance to be used. Moreover, with respect to the window function, a suitable value can be selected from a list of values according to the number of candidate points and distribution of candidate points.

In order to further make it correspond to the existing range of the puncture-needle 3, the extraction density of candidate points for every range of a predetermined size can be obtained, and if the density of the range is equal to a predetermined rate or greater as compared with the density of the range including the weighting average position, the emphasis level can be set not to be decreased. Especially, in a case where the puncture-needle 3 is included in the image used for making diagnosis by passing through one end of the image used for making diagnosis, it can be set not to suppress the emphasis level of the puncture-needle 3 from the weighting average position to the one end. Alternatively, since the number of candidate pints on the candidate line L usually is to be greater as the existing range of the puncture-needle 3 be longer, there can be set a range where the emphasis level is not to be decreased according to the number of candidate points or the window width of the filter can be changed.

Further, in a case where the extraction range and the non-extraction range of candidate points are clearly divided by the above method, this border can simply be the tip of the punctuation-needle 3. Further, by using another method or in combination with another method, the tip position can be estimated and the window width according to the length between the weighting average position and the estimated tip position can be set.

Figure 7:
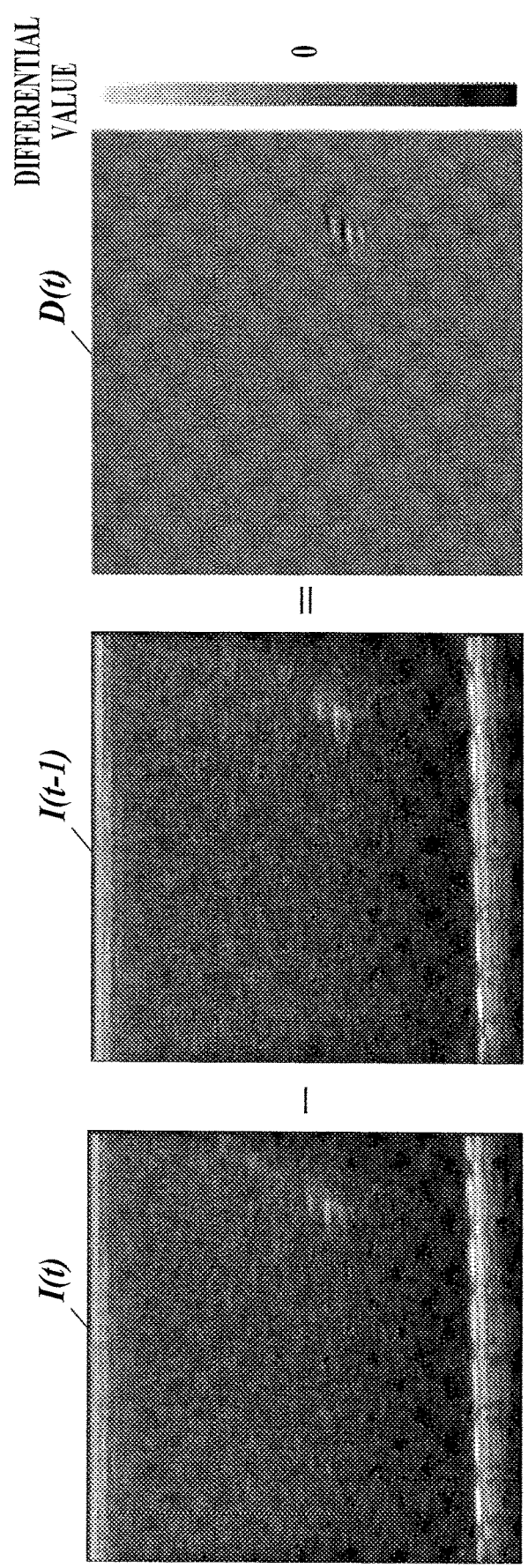
FIG. 7 is a view showing an example relating to estimation of the tip position of a puncture-needle.

FIG. 7 is a view showing an example relating to estimation of the tip position of the puncture-needle 3.

In a case where there are two images for making diagnosis (t) and I(t−1) which are obtained at different timings while the puncture-needle 3 is being inserted in to a subject who is basically not moving, by generating a difference image D(t) of these two images, only the tip portion of the moved puncture-needle 3 appears as non-zero differential value.

Figure 8:
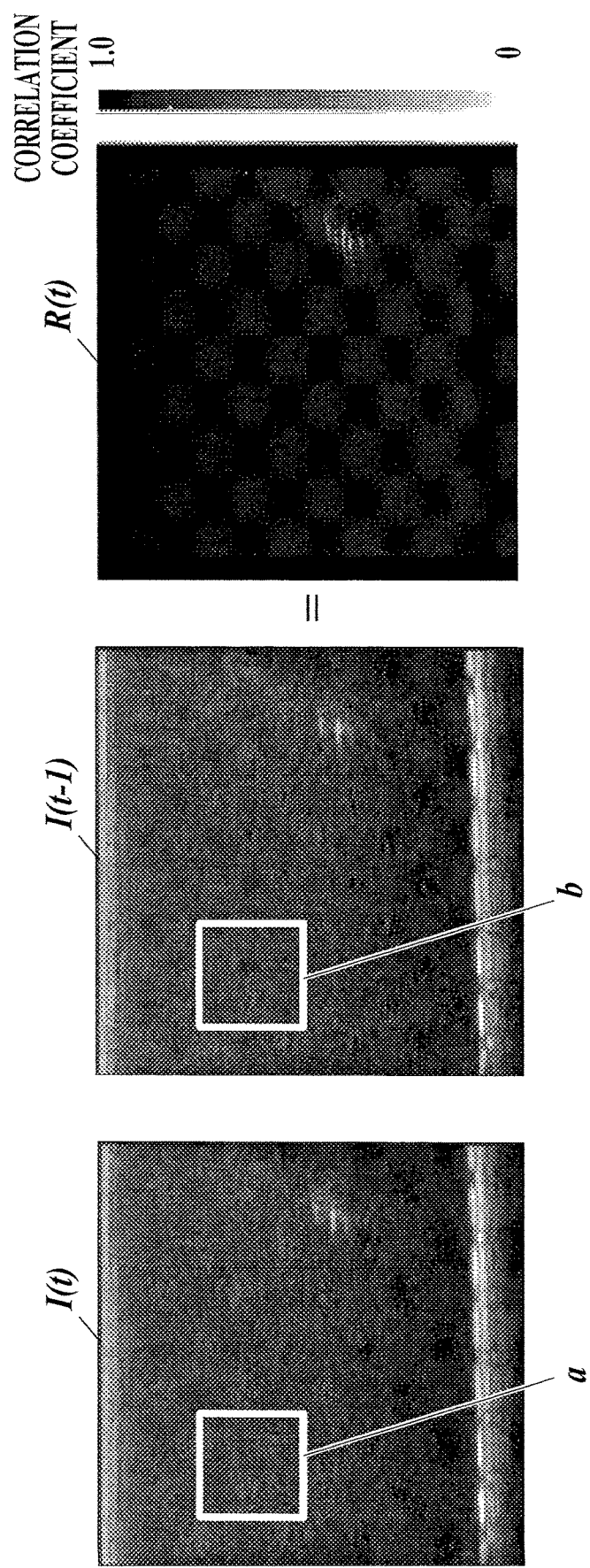
FIG. 8 is a view showing the second example relating to estimation of the tip position of a puncture-needle.

FIG. 8 is a view showing the second example relating to estimation of the tip position of the puncture-needle 3.

Here, correlation of the pixel values in a predetermined size regions set in the plurality of frames of the images used for making diagnosis is taken to obtain the correlation map image R(t) showing the distribution of the correlation values. For example, the concern region a(x, y, t) of a predetermined size in the image used for making diagnosis I(t) having the coordinates (x, y) as the center thereof, is set for the coordinates (x, y) of each pixel position, the concern region b(x, y, t−1) of the same size in the previous image used for making diagnosis I(t−1), having the coordinates (x, y) as the center, is set, and the correlation coefficient r(x, y, t) (cross-correlation coefficient) is calculated by using the pixel values in the regions a and b. If the puncture-needle 3 moves, the correlation coefficient (x, y, t) of the concern regions a and b including the moving region is to be small. Thus, the tip position of the puncture-needle 3 is estimated.

Figure 9:
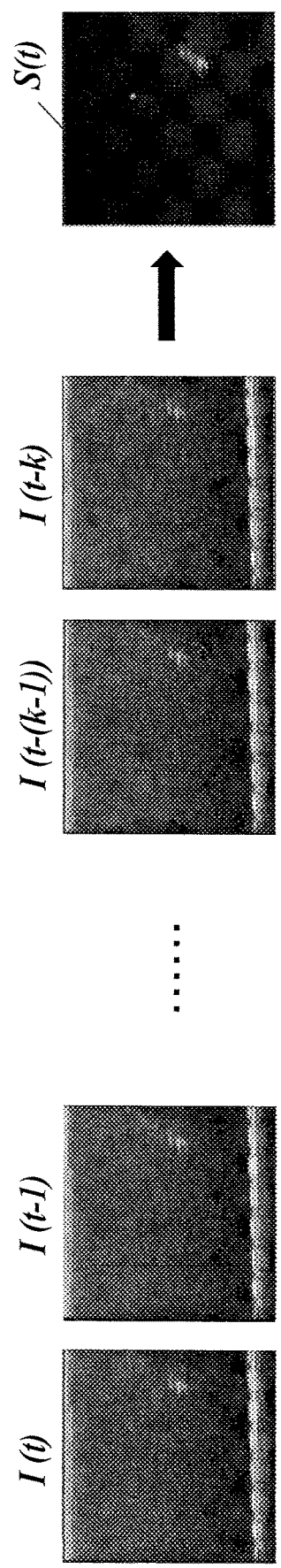
FIG. 9 is a view showing the third example relating to estimation of the tip position of a puncture-needle.

FIG. 9 shows a view of the third example relating to estimation of the tip position of the puncture-needle 3.

Here, the variances of the pixel values at the same pixel position in the images used for making diagnosis I(t) to I(t−k) which are taken over few times (k+1) at different timings are calculated to generate the pixel value variance image S(t). Here, standard deviation can be used instead of variance. As a result, in the images used for making diagnosis (t) to I(t−k) the moving path of the puncture-needle 3 has their pixel values (brightness) changed temporarily and the variances are to be large, and thus, the tip position of the puncture-needle 3 is estimated.

FIG. 10 shows the fourth example relating to estimation of the tip position of the puncture-needle 3.

Here, the variance image SD(t) is obtained using (k+1) frames of difference images D(t) formed of a difference value between different frames shown in FIG. 7. That is, variances of pixel values at the same pixel position in k sheets of difference images D(t) to D(t−k) are calculated, and the tip position of the puncture-needle 3 is estimated from the position where the non-zero variance exits.

In a case where the tip position of the puncture-needle 3 is estimated by the above image processing, a window can be set so as to suppress decreasing in emphasis level from the weighting average position to the estimated tip position and so that the decreasing of emphasis level be greater in the region that is on the side of the tip position that is opposite of the weighting average position. For example, in a case where the tip position can be obtained with relatively high accuracy, the window function used for setting the emphasis range and the emphasis level can be a rectangular window or a window close to rectangle.

Figure 11A:
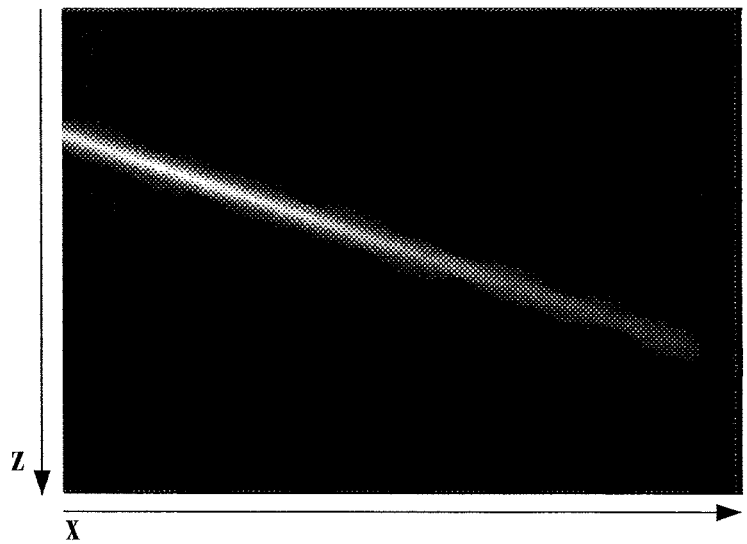
FIG. 11A is a view showing an emphasis display example of the position of the identified puncture-needle.
Figure 11B:
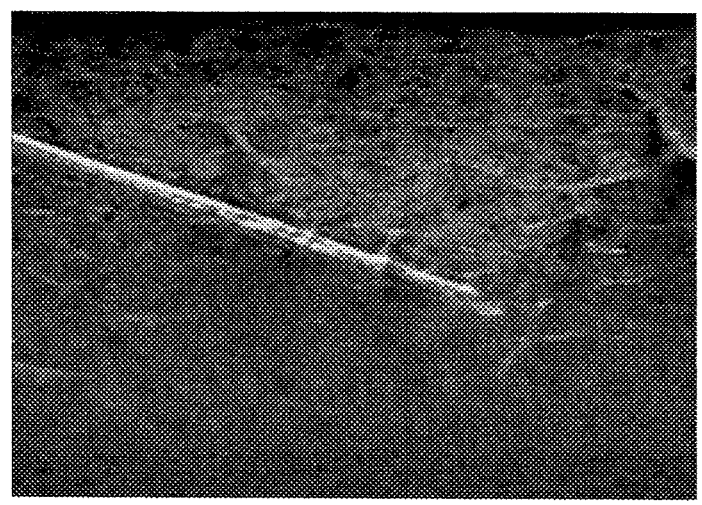
FIG. 11B is a view showing an example of an output image which is formed by overlapping the emphasis display of the puncture-needle on the original image used for making diagnosis.

FIGS. 11A and 11B show examples of emphasis display of the puncture-needle 3 position which is identified by the ultrasound diagnosis apparatus U of the embodiment.

The emphasis level set in FIG. 5D is suppressed according to distribution (gathering condition) of the candidate points on the candidate line L. In the right side of the image used for making diagnosis, it is set so that the emphasis display be lighter as shown in FIG. 11A. Then, this emphasis display is overlapped on the original image used for making diagnosis and the output image is generated (FIG. 11B). This emphasis display can be in a color (for example, blue or the like) different from the color of the original image used for making diagnosis (for example, black and white display) so that the emphasis display can be seen clearly.

FIG. 12 is a flowchart showing the controlling procedure of the puncture-needle detection emphasis process carried out in the ultrasound diagnosis apparatus U according to the embodiment.

As described above, this process is executed by the CPU of the controller 11 or the image processor 16.

When the puncture-needle detection display process starts, the CPU makes the detection map generator 162 calculate the feature amount sc of each pixel position in the two-dimensional structure image (image used for making diagnosis) of a subject which is obtained in a similar manner as obtaining a regular-mode and store the feature amount sc so as to be related with pixel position information (step S101). The CPU further processes the feature amounts sc to obtain partial differential values ds to generate the detection map data of the puncture-needle 3 (step S102). The CPU compares the individual values on the detection map data to a predetermined standard value, and extracts candidate points in the range of the puncture-needle 3.

The CPU makes the puncture-needle identifier 163 carry out Hough transform on the extracted candidate points and detect a straight line (step S111). The CPU determines a candidate line which is the candidate for the puncture-needle 3 in the detected straight line (step S112). At this time, the CPU also specifies the tip position of the puncture-needle 3 if possible. The CPU determines the emphasis level which is to be the standard for carrying out emphasis display of the candidate line (step S113).

The CPU makes the emphasis processor 164 calculate parameters relating to position, range and emphasis level for carrying out emphasis display (step S121). With respect to the candidate line, the CPU determines the suppression pattern in the emphasis range according to the plausibility of the range corresponding to the puncture-needle 3 (step S122). The CPU generates the emphasis map reflecting the determined suppression pattern (step S122) and overlaps the generated emphasis map on the original image used for making diagnosis (step S124). Then, the CPU stores the ultrasound image in which the puncture-needle 3 is emphasized in the storage unit 161 and ends the puncture-needle detection emphasis process.

As described above, the ultrasound diagnostic apparatus U of the embodiment is an ultrasound diagnostic apparatus U which generates an ultrasound image of inside of a subject on the basis of received ultrasound signals which reflected off at inside the subject. The ultrasound diagnostic apparatus U includes the detection map generator 162 and the puncture-needle identifier 163 as the needle position specifier and the emphasis processor 164. As the needle position specifier, the detection map generator 162 and the puncture-needle identifier 163, with respect to each region of an ultrasound image, obtains the maximum value of brightness which is the deep region feature value relating to the signal intensity in the region deeper than the region subject to judgment and the average value of brightness which is the shallow region feature value relating to the signal intensity in the region shallower than the region subject to judgment in relation to distribution of ultrasound signals along the emission direction of ultrasounds that enters the subject, and then, determines the position of the puncture-needle 3 which is inserted inside the subject on the basis of the deep region feature value and the shallow region feature value. The emphasis processor 164 carries out the process for emphasizing the needle position range in an ultrasound image.

The position of the puncture-needle 3 which is the border of the shadow region can be determined more easily due to decrease in brightness in the shadow region (acoustic shadow) that is produced by the puncture-needle 3 when ultrasound signals enter. Therefore, the puncture-needle 3 can be detected easily and accurately without complicating the structure and the processing as compared with those in conventional techniques.

Further, even in a case where another structure on which ultrasounds reflect off exists, the position of the puncture-needle 3 can be determined more accurately as compared with conventional techniques by using the border of the shadow region at the position of the puncture-needle 3.

The detection map generator 162 determines the position of the puncture-needle 3 inserted inside the subject Q on the basis of the feature amount sc, the feature amount sc being the difference of the shallow region feature value and the deep region feature value. Therefore, without complicating the process, the position of the puncture-needle 3 can be determined in the distribution of ultrasound intensity across the region where ultrasounds enter normally and the region that is to be in the shadow of the puncture-needle 3 by using a simple calculation.

The detection map generator 162 determines the position of the puncture-needle 3 inserted inside the subject Q on the basis of the partial differentiation values ds which are values relating to rate of variability in relation to the difference of the shallow region feature value and the deep region feature value in the depth direction. Therefore, the position of the puncture-needle 3 can be determined accurately by easily and accurately detecting the discontinuity in the feature amounts sc at the border of shadow produced by the puncture-needle 3 as a line.

The detection map generator 162 obtains any one of average value, the most frequent value or the median of values corresponding to the signal intensity at individual regions in the region shallower than the region subjected to judgment as the shallow region feature value. By using such statistical value representing the shallow region as the shallow region feature value, the process can be simplified and the position of the puncture-needle 3 can be determined appropriately and easily in the overall distribution of ultrasound signals.

The detection map generator 162 obtains the maximum value of values corresponding to signal intensity at individual regions in the region deeper than the region subjected to judgment as the deep region feature value. Therefore, whether or not the shadow of the puncture needle 3, which is at the position deeper than the position of the puncture-needle 3, represents only the region where ultrasound intensity is decreased can be determined easily by using the deep region feature value.

The detection map generator 162 extracts a plurality of candidate points where the difference of the deep region feature values and the shallow region feature values thereof fulfill a predetermined condition, and determines the position of the puncture-needle 3 on the basis of the plurality of candidate points. That is, since candidate points can be extracted easily and more accurately as compared with the conventional techniques, the position of the puncture-needle 3 can be determined accurately using the candidate points.

Further, since the plurality of candidate points are set for every pixel unit in an ultrasound image, the processes relating to identification and emphasizing of the puncture-needle 3 can be carried out easily in the structure similar to that of a normal image processing.

The ultrasound diagnosis apparatus U further includes the transducer allay 21 which transmits and receives ultrasound signals and the controller 11 (CPU) which controls the transmission/reception range of the transducer array 21. When obtaining an ultrasound image, in which the detection map generator 162 extracts a plurality of candidate points and the puncture-needle identifier 163 identifies the puncture-needle 3 and determines the position thereof, the controller 11 makes the width for entering ultrasounds in the width direction that is orthogonal to the length direction of the puncture-needle 3 be narrower as compared with that when the ultrasound image is obtained by not extracting a plurality of candidate points and not determining the position of the puncture-needle 3.

Therefore, only in the case where image pickup of the puncture-needle 3 is to be carried out, by making the transmission width of ultrasounds narrow so that the S/N ratio will not be degraded by the ratio of the ultrasound intensity which transmits along the sides of the puncture-needle 3 and the ultrasound intensity whose transmission is blocked by the puncture-needle 3, suitable ultrasounds according to an appropriate image with concern not to cause deterioration in image quality and sensitivity in a normal image obtaining and sensitivity required by the puncture-needle 3 can be output.

Further, since the position of the puncture-needle 3 is determined assuming that the shape of the puncture-needle 3 which is to be identified is a straight line, a suitable straight line can be detected easily and the puncture-needle 3 can be identified by detecting the candidate points which are arranged in a straight line on the detection map on the basis of the extracted candidate points.

Second Embodiment

Next, the second embodiment of the ultrasound diagnosis apparatus of the present invention will be described.

The configuration of the ultrasound diagnosis apparatus U of the second embodiment is the same as that of the ultrasound diagnosis apparatus U of the first embodiment. The same symbols are used for similar units and their descriptions are omitted.

Next, the detection method of the puncture-needle 3 in the ultrasound diagnosis apparatus U of the second embodiment will be described.

In the ultrasound diagnosis apparatus U of the second embodiment, the position of the puncture-needle 3 is detected by mainly using the deep region feature value.

Figure 13A:
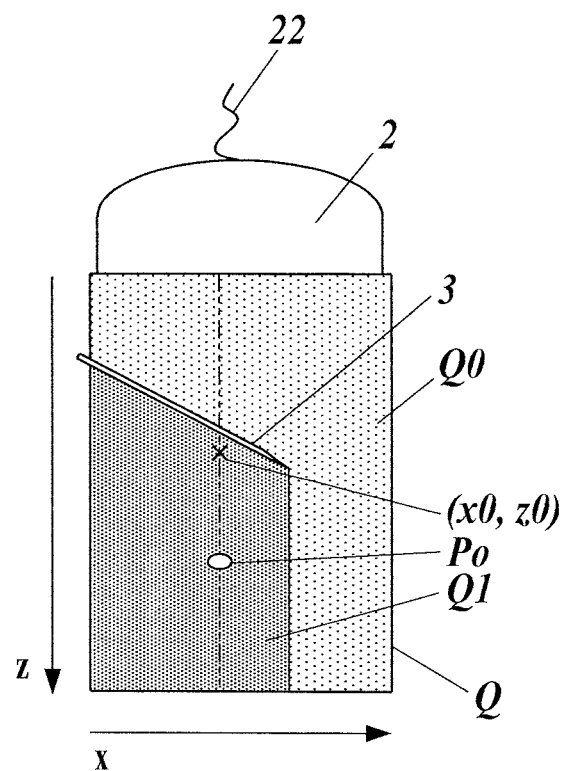
FIG. 13A is a schematic view showing a pattern example of an image used for making diagnosis with respect to the depth direction.
Figure 13B:
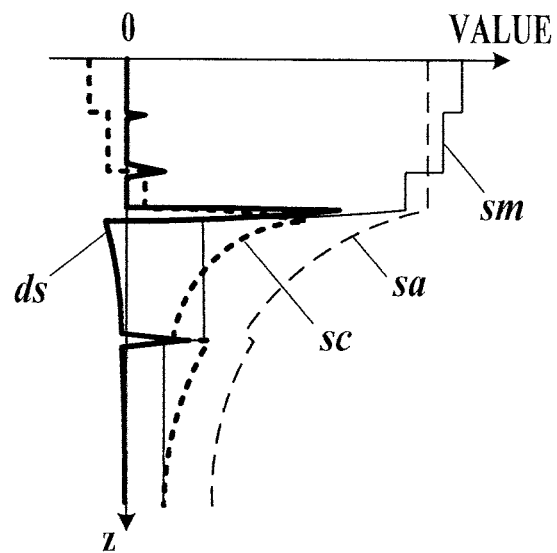
FIG. 13B is a schematic view showing a modification example of the shallow region feature value, deep region feature value, feature amount and partial differential value with respect to the depth direction.

FIGS. 13A and 13B are schematic views showing deformation example of the shallow region feature value sa, the deep region feature value sm, the feature amount sc and the partial differential value ds with respect to the depth direction.

As described above, at the region deeper than the puncture-needle 3, there does not exist a part where reflection intensity is large due to the acoustic shadow. As a result, at the region deeper than the position of the puncture-needle 3, the deep region feature value sm decreases drastically due to the maximum value decreasing drastically. On the other hand, the shallow region feature value sa decreases gradually in relation to the depth at the region deeper than the position of the puncture-needle 3.

Therefore, as it can be clearly seen in FIG. 13B, the deep region feature value sm is greatly effective with respect to increase in the partial differential value ds, and the partial differential value ds can obtain the maximum value at the position of the puncture-needle 3 also by the partial differential value $dsm=\partial sm/\partial z=sm(x0, z0)-sm(x0, z0-1)$ of the deep region feature value sm in the depth direction.

However, in a case where exists a ultrasound reflecting source Po other than the puncture-needle 3, especially in a case where the reflecting source Po is in the region deeper than the puncture-needle 3 as shown in FIG. 13A, a position where the partial differential value dsm be a great value other than the position of the puncture-needle 3 is easily produced as shown in FIG. 13B. Although noises and local reflecting sources are usually removed when a candidate line is extracted by Hough transform, it is difficult to differentiate in a case especially where an object in the form of straight line such as a bone is the reflecting source of ultrasound. Therefore, in the ultrasound diagnosis apparatus U of the second embodiment, the shallow region feature value sa is used as a supplement in the above described case.

As a method for using the shallow region feature value sa as a supplement, for example, a method where the above described partial differential value dsm is multiplied by the shallow region feature value sa or the shallow region feature value sa is added to (subtracted from) the above described partial differential value dsm can be suggested. At this time, the partial differential value dsm and the shallow region feature value sa can be multiplied by a predetermined coefficient α in order to change the rate of influence to the partial differential value dsm. Since the insertion position of the puncture-needle 3 is in a range shallower than the position of a bone, the puncture-needle 3 and the bone can be differentiated by the partial differential value dsm being corrected so that the feature amount be relatively small in the deep region where the shallow region feature value sa is small. In the ultrasound diagnosis apparatus U of the embodiment, the position of the puncture-needle 3 is identified by using equations such as feature amount $sc2=sa\times(-dsm)$ and feature amount $sc3=\alpha\times sa-dsm$.

Figure 14A:
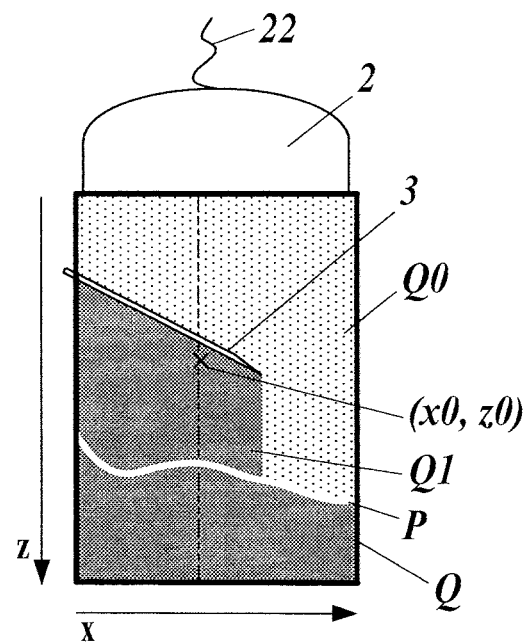
FIG. 14A is a schematic view showing another pattern example of an image used for making diagnosis with respect to the depth direction.
Figure 14B:
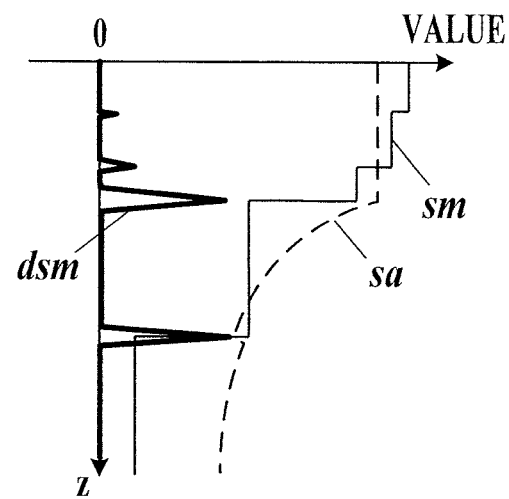
FIG. 14B is a schematic view showing a modification example of the shallow region feature value, deep region feature value and partial differential value with respect to the depth direction.
Figure 14C:
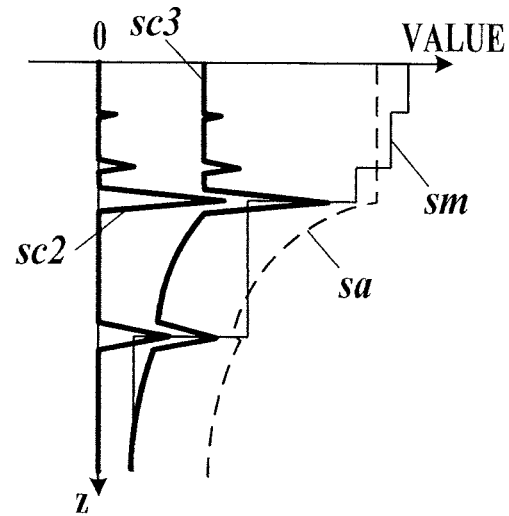
FIG. 14C is a schematic view showing a modification example of the shallow region feature value, deep region feature value and feature amount with respect to the depth direction, the feature amount being obtained in the ultrasound diagnosis apparatus of the second embodiment.

FIGS. 14A to 14C are schematic view showing deformation examples of the shallow region feature value sa, the deep region feature value sm, the partial differential value dsm and the feature amounts sc2 and sc3 with respect to the depth direction.

In a case where a bone P exits at a position deeper than the position of the puncture-needle 3 as shown in FIG. 14A, there is a possibility that ultrasounds concentrate and reflect off at this position. Therefore, ultrasound intensity become large and as a result, the deep region feature value sm drops greatly at two points, at the position of the puncture-needle 3 and at the position of the bone P as shown in FIG. 14B, and there may be a case where it is difficult to distinguish which of the maximum values of the partial differential value dsm is the position of the puncture-needle 3. Further, if the length of the part that extends in the form of straight line becomes longer, it is difficult to appropriately specify the candidate line by using Hough transform.

At this time, by calculating the feature amounts sc2 and sc3 as showing in FIG. 14C, with respect to the peak values of the equal partial differential value dsm, the weight according to the shallow region feature value sa is to be smaller (lighter) as the position is to be deeper, and a difference is produced between the feature amounts sc2 and sc3. Therefore, the position of the puncture-needle 3 can be identified more easily and accurately due to the difference.

As described above, the ultrasound diagnosis apparatus U is an ultrasound diagnosis apparatus U which generates an ultrasound image of inside of a subject Q on the basis of ultrasound signals which are reflected off at inside of the subject and received. The ultrasound diagnosis apparatus U includes the detection map generator 162 and the puncture-needle identifier 163 as the needle position specifier and the emphasis processor 164. As the needle position specifier, the detection map generator 162 and the puncture-needle identifier 163, obtains the deep region feature value sm relating to signal intensity in the region deeper than the region subject to judgment with respect to each region in an ultrasound image in relation to ultrasound signal distribution along the entering direction of ultrasounds that are emitted in to the subject Q, that is, along the depth direction of the subject Q, and specifies the position of the puncture-needle 3 which is inserted inside of the subject Q on the basis of the deep region feature value sm. The emphasis processor 164 carries out the processes for emphasizing the needle position range in the ultrasound image.

The position of the puncture-needle 3 can be determined more easily by the partial differential value dsm which deforms appropriately according to the border of the shade region reflecting the decrease in brightness in the shadow region (acoustic shadow) that is produced by the puncture-needle 3. Therefore, the puncture-needle 3 can be detected easily and accurately without complicating the structure and the processing as compared with those in conventional techniques.

The needle position specifier (the detection map generator 162 and the puncture-needle identifier 163) sets the partial differential value dsm which is a value related to the rate of variability of the deep region feature value sm in the emission direction as a predetermined feature amount, and specifies the position of the puncture needle 3 on the basis of the predetermined feature amount. Therefore, the puncture-needle 3 can be detected easily and appropriately by appropriately extracting the border of the shadow by using the partial differential value dsm.

Further, the detection map generator 162 and the puncture-needle identifier 163 sets the product of the partial differential value dsm, which is a value related to the rate of variability of the deep region feature value sm, and the shallow region feature value sa as the predetermined feature amount sc2, and determines the position of the puncture-needle 3 on the basis of the feature amount sc2. In such way, by the shallow region feature value sa being used supplementary as the weighting coefficient to the deep region feature value sm, the position of the puncture needle 3 can be specified more easily and accurately.

Alternatively, the detection map generator 162 and the puncture-needle identifier 163 sets the sum of the partial differential value dsm which is a value related to the rate of variability of the deep region feature value sm and the product of the shallow region feature value sa and the predetermined coefficient α (multiplied by a predetermined coefficient) as the predetermined feature amount sc3, and determines the position of the puncture-needle 3 which is inserted inside a subject on the basis of the feature amount sc3. In such case, by the shallow region feature value sa also being used as a supplement, the position of the puncture-needle 3 can be specified by using the deep region feature value sm more easily and accurately.

The present invention is not limited to the above described embodiment, and can be modified in various ways.

For example, although the puncture-needle 3 is identified by extracting candidate points in pixel units in the above described embodiment, units larger than pixels can be set as the minimum units and a process for decreasing random noise and the like can be also used to detect the puncture-needle 3.

Further, although a straight line corresponding to the shape of the puncture-needle 3 is detected by using Hough transform in the above described embodiment, a straight line can be detected by using other method. Alternatively, the border position where the deep region feature value and the shallow region feature value change can be the position of the puncture-needle 3 as it is or the border position can be connected by a curved line to be set as the position of the puncture-needle 3, without temporarily specifying a straight line. Even if the shape of the puncture-needle 3 is not a straight line, a region having a shape corresponding to the shape of the puncture-needle 3 is detected.

In the above described embodiment, the average value of brightness in the region shallower than the pixel which is subject to judgment (or a statistical value which represents brightness distribution such as a median or a mode) and the maximum value of brightness in the region deeper than the pixel which is subject to judgment are used. However, this is not limitative in any way. An average value can be used with respect to brightness in the deep region or an average value of a plurality of pixels can be used instead of merely the maximum value. Alternatively, an appropriate value can be selected according to the position where the image used for making diagnosis is obtained. Further, although all of the pixels along the emission direction of ultrasounds in a range in the image used for making diagnosis are equally used to calculate the average value and the maximum value thereof in the above embodiment, they can be weighted.

Although the difference of the adjacent pixels is simply obtained as the partial differential value in the above embodiment, an average value of a forward difference and a backward difference can be used or an average amount of change of a plurality of pixels can be obtained and used.

In the above embodiment, the partial differential values ds are binarized to be set as the candidate points of the position of the puncture-needle 3 and a straight line is detected by using the candidate points. However, it is not limited to binarization, and the candidate points can be obtained by the relation with partial differential values ds between adjacent pixels or between pixels along the emission direction of ultrasounds. Alternatively, pixel positions judged as not corresponding to the position of the puncture-needle 3 can be omitted as needed while calculating the partial differential values ds and not carrying out the process in two stages.

In a case where a structure that is clearly not related to the shadow is included in the image used for king diagnosis from the beginning, detection of the puncture-needle 3 can be carried out after such structure is removed or after performing filtering or the like.

In the second embodiment, the shallow region feature value sa is used supplementary when the position of the puncture-needle 3 is difficult to be decided by using the deep region feature value sm. However, the above process can be carried out by using the deep region feature value sm and the shallow region feature value sa from the beginning to specify the position of the puncture-needle 3 more accurately.

Other than the above, the specific structures, details of the processing content and procedures can be modified s needed within the scope of the invention.

This U.S. patent application claims priority to Japanese patent applications No. 2015-002775 and No. 2015-248101 respectively filed on Jan. 9, 2015 and Dec. 21, 2015, the entire contents of which are incorporated by reference herein for correction of incorrect translation.

What is claimed is:

1. An ultrasound apparatus comprising:
   an image generator which generates an ultrasound image of an inside of a subject based on ultrasound signals which are reflected off at the inside of the subject and received;
   a needle position specifier which, with respect to each region in the ultrasound image, obtains a deep region feature value relating to signal intensity in a region deeper than a region subject to judgment in relation to an ultrasound signal distribution along an emission direction of the ultrasound signals emitted in the subject, and which specifies a position of a puncture-needle which is inserted in the subject based on a shadow region produced by the puncture-needle when the ultrasound signals enter the subject;
   a needle emphasis processor which carries out a process for emphasizing the position of the puncture-needle which is specified in the ultrasound image by processing the ultrasound image to clarify an appearance of the puncture-needle in the ultrasound image; and
   a display which displays the ultrasound image in which the appearance of the puncture-needle has been clarified by the processing carried out by the needle emphasis processor.

2. The ultrasound apparatus according to claim 1, wherein the needle position specifier sets a value relating to a rate of variability of the deep region feature value in the emission direction as a predetermined feature amount, and specifies the position of the puncture-needle based on the predetermined feature amount.

3. The ultrasound apparatus according to claim 1, wherein the needle position specifier obtains the deep region feature value and a shallow region feature value relating to signal intensity in a region shallower than the region subject to judgment, and specifies the position of the puncture-needle based on the deep region feature value and the shallow region feature value.

4. The ultrasound apparatus according to claim 3, wherein the needle position specifier sets a product of a value relating to a rate of variability of the deep region feature value in the emission direction and the shallow region feature value as a predetermined feature amount, and specifies the position of the puncture-needle based on the predetermined feature amount.

5. The ultrasound apparatus according to claim 3, wherein the needle position specifier sets a sum of a value relating to a rate of variability of the deep region feature value in the emission direction and a value obtained by multiplying the shallow region feature value by a predetermined coefficient as a predetermined feature amount, and specifies the position of the puncture-needle based on the predetermined feature amount.

6. The ultrasound apparatus according to claim 3, wherein the needle position specifier sets a difference between the deep region feature value and the shallow region feature value as a predetermined feature amount, and specifies the position of the puncture-needle based on the predetermined feature amount.

7. The ultrasound apparatus according to claim 6, wherein the needle position specifier specifies the position of the puncture-needle based on a value relating to a rate of variability of the predetermined feature amount in the emission direction.

8. The ultrasound apparatus according to claim 3, wherein the needle position specifier obtains one of an average value, a most frequent value, and a median of values relating to signal intensity in individual regions shallower than the region subject to judgment as the shallow region feature value.

9. The ultrasound apparatus according to claim 1, wherein the needle position specifier obtains a maximum value of values relating to signal intensity at individual regions deeper than the region subject to judgment as the deep region feature value.

10. The ultrasound apparatus according to claim 2, wherein the needle position specifier extracts a plurality of regions whose predetermined feature amounts fulfill a predetermined condition as detection candidate regions, and specifies the position of the puncture-needle based on the detection candidate regions.

11. The ultrasound apparatus according to claim 10, wherein the plurality of detection candidate regions are set in pixel units of the ultrasound image.

12. The ultrasound apparatus according to claim 1, further comprising:

a transceiver which performs transmission and reception of the ultrasound signals; and a controller which controls a transmission and reception range of the transceiver, wherein the controller controls such that a width where the ultrasound signals are to be emitted in a width direction perpendicular to a length direction of the puncture-needle is narrower when obtaining the ultrasound image with respect to which the needle position specifier specifies the position of the puncture-needle as compared to the width where the ultrasound signals are to be emitted when obtaining an ultrasound image not used to specify the position of the puncture-needle.

13. The ultrasound apparatus according to claim 1, wherein a shape of the specified puncture-needle is a straight line.

14. The ultrasound apparatus according to claim 1, wherein the needle position specifier specifies the position of a puncture-needle which is inserted in the subject based on a border of the shadow region.

15. The ultrasound apparatus according to claim 1, wherein the needle emphasis processor emphasizes the position of the puncture-needle which is specified in the ultrasound image by overlapping an emphasis image over the ultrasound image, a color of the emphasis image being different from a color of the ultrasound image.

* * * * *